United States Patent [19]

Causey, III

[11] Patent Number: 5,425,373
[45] Date of Patent: Jun. 20, 1995

[54] APPARATUS AND METHOD FOR ANALYZING AND ENHANCING INTERCARDIAC SIGNALS

[75] Inventor: James D. Causey, III, Simi Valley, Calif.

[73] Assignee: Pacesetter, Inc., Sylmar, Calif.

[21] Appl. No.: 181,330

[22] Filed: Jan. 14, 1994

Related U.S. Application Data

[63] Continuation of Ser. No. 967,915, Oct. 28, 1992, abandoned, which is a continuation of Ser. No. 641,382, Jan. 15, 1991, abandoned.

[51] Int. Cl.$^6$ ............................................. A61B 5/0402
[52] U.S. Cl. ..................................... 128/697; 607/27
[58] Field of Search .................... 128/697; 607/27, 30, 607/31

[56] References Cited

U.S. PATENT DOCUMENTS

| | | | |
|---|---|---|---|
| 3,871,363 | 5/1975 | Day | 128/419 OPT |
| 4,250,888 | 2/1981 | Grosskopf | 128/702 |
| 4,476,869 | 10/1984 | Bihn | 128/419 OPT |
| 4,791,936 | 12/1988 | Snell et al. | 128/419 OPT |
| 4,809,697 | 11/1987 | Causey, III et al. | 128/419.0 PT |
| 4,812,976 | 3/1989 | Lundy | 128/697 |
| 4,979,506 | 12/1990 | Silvian | 607/31 |
| 5,020,540 | 6/1991 | Chamoun | 128/698 |

*Primary Examiner*—William E. Kamm
*Attorney, Agent, or Firm*—Lisa P. Weinberg

[57] ABSTRACT

An external diagnostic/programming device is disclosed which includes means for both displaying intracardiac electrical signals sensed and telemetered from an implantable pacemaker in real-time, and for storing the intracardiac electrical signals for subsequent retrieval and analysis. The subsequent analysis selectively includes processing means for processing the signals off-line (i.e., not in real-time), using various signal processing strategies, such as digital filtering and frequency domain spectral analysis. The off-line signals may also be recursively processed in order to enhance the detection of a particular physiologic phenomena manifested by, but not readily discerned within, the unprocessed real-time signals.

35 Claims, 6 Drawing Sheets

APPARATUS AND METHOD FOR ANALYZING AND ENHANCING INTERCARDIAC SIGNALS

CROSS REFERENCE

This specification is a Continuation of application Ser. No. 07/967,915, filed Oct. 28, 1992 (now abandoned), which is a Continuation of application Ser. No. 07/641,382, filed Jan. 15, 1991 (also now abandoned).

FIELD OF THE INVENTION

The present invention relates generally to implantable pacemakers, and more particularly to apparatus and methods for analyzing intracardiac electrical data obtained from an implantable pacemaker and/or a surface (skin) electrocardiographic signal. Even more particularly, the present invention relates to a system which acquires intracardiac electrical data from an implantable pacemaker, stores it, and then subsequently processes it in accordance with at least one of a plurality of non-real-time signal processing strategies. These signal processing strategies are selected to enhance the observability and detectability of the informational content of the intracardiac electrical data.

BACKGROUND OF THE INVENTION

In recent years, most implantable pacemakers have included the capability of transmitting an intracardiac electrical signal (e.g., P-waves, R-waves, etc.), either alone or in combination with marker signals. The intracardiac electrical signal provides data indicative of heart activity, including the contraction of the atria as sensed by the pacemaker sensing circuits, the contraction of the ventricles as also sensed by the pacemaker sensing circuits, and the timing therebetween. Further, if stimulation pulses are generated by the pacemaker in order to cause a particular heart chamber to contract at a particular time, such is also evident in the intracardiac electrical data telemetered from the pacemaker. As used herein, the intracardiac electrical data includes the intracardiac electrical signals and any marker data.

The display or printing of the intracardiac electrical signal as a function of time is known as an intracardiac electrogram, EGM or IEGM. Advantageously, the intracardiac EGM provides a "picture" of the performance of the heart and pacemaker. Any problems associated with the heart, or with the pacemaker, are usually evident from an analysis of the intracardiac EGM. If intracardiac electrical data is not available, then a conventional surface electrocardiographic signal may be made using, e.g., skin electrodes. As used herein, display or printing of the surface electrocardiographic signals as a function of time is known as a surface electrocardiogram, or ECG. The surface ECG also provides a "picture" of the performance of the heart and a pacemaker.

Because special equipment must be used to record a surface ECG, it is generally preferred for a patient already having an implanted pacemaker to utilize the intracardiac electrical data from the pacemaker as the primary indicator of the heart's performance. To this end, some pacemaker manufacturers include as an integral part of their diagnostic and programming devices (used by the physician or cardiologist to program and interrogate the implanted pacemaker), the ability to print and/or display the intracardiac electrical data received from the pacemaker as a function of time.

Such intracardiac electrical data, when printed or displayed as a function of time, appears dissimilar to a surface ECG. (It is noted that the shape of some of the waveforms included within the intracardiac electrical data, e.g., a P-wave, representing contraction of the atria, or an R-wave, representing contraction of the ventricles, may appear somewhat distinct from the shape of corresponding waveforms included within a surface electrocardiographic signal due to the different location from which such signals are sensed, one being sensed from inside the heart, the other being sensed at the skin of the patient. However, the timing relationship between such waveforms remains approximately the same.)

Further, some recent diagnostic/programming devices (frequently referred to as "programmers") include the ability to "freeze" the incoming intracardiac electrical data so that the displayed intracardiac EGM may be carefully studied. An example of a diagnostic/programming device which includes the capability of displaying, printing and freezing the incoming intracardiac electrical data is described in applicant's earlier U.S. Patent No. 4,809,697, to Causey, III et al., which patent is hereby incorporated herein by reference. It should also be noted that the diagnostic/programming device described in the referenced patent also includes the capability of selectively displaying the surface electrocardiographic signal as well as intracardiac electrical data.

It is not uncommon when observing intracardiac electrical data or surface electrocardiographic signals on a programming device, or equivalent display, for "noise" to mask out important features of the waveform being studied. (As used herein, the term "noise" refers to any unwanted signal.) When this occurs, it is necessary to identify the source of the noise, if it is identifiable, and then make attempts to eliminate the source of the noise, or at least minimize its effect.

For example, there may be a 60 Hz component present in the waveform which originates with the line power. If this occurs, attempts must be made to filter out the 60 Hz component before it interacts with the circuits displaying the intracardiac electrical data or surface electrocardiographic signal. Once this is successfully done, the intracardiac electrical data or surface elecardiographic signal (in the absence of the 60 Hz background noise) may be retaken. Having to retake such data, however, is not only inconvenient and possibly stressful for the patient, but is also expensive to perform.

Unfortunately, some types of noise are not specific to a particular frequency, and may not originate from any one source. Hence, it is difficult to separate such noise from the incoming data without also compromising the integrity of the incoming data. In such instances, it is usually necessary to apply one or more different kinds of filters to the incoming data in an attempt to remove the noise without adversely impacting the integrity of the signal. Unfortunately, this typically requires a time-consuming iterative process wherein a particular filter type is selected prior to gathering the intracardiac electrical data, after which the data is gathered and evaluated.

Then, based on the results of the evaluation, another filter type is selected (or the prior filter type is modified), and additional data is gathered and evaluated. This process is repeated as many times as is necessary in order to optimize the intracardiac electrical data so that any cardiac phenomena manifested therein can best be detected and observed. Disadvantageously, such an iterative process is not only expensive (both in terms of time consumed, as well as in the costs associated with the design, fabrication and test of the various signal processing elements, e.g., filters which must be used), but it is also bothersome and stressful to the patient. What is needed, rather, is a system wherein the intracardiac electrical data or surface elecardiographic signal can be acquired once, and thereafter processed as many times as desired using inexpensive, flexible signal processing methods and techniques.

As is evident from the above description, one of the problems associated with monitoring the performance of implanted products through telemetry and/or surface patient connections is that the data is typically displayed in real-time. Because real-time data is only present for an instant of time, it is thus common to "capture" or "freeze" the data by printing it and/or by storing it in memory for subsequent display. However, as the real-time data is thus captured or frozen, a desired signal processing technique must be applied, e.g., filtering, in order to remove any unwanted signals or interference as the data is captured.

The use of such real-time signal processing techniques commonly introduces distortion which denies the accurate reproduction of the signal of interest. While many sophisticated signal processing circuits are known in the art which could be used to process a given signal in real-time for a particular purpose, such circuits are complex and expensive to make and operate. Further, if the intracardiac electrical data is to be processed in real-time for more than one purpose, it is typically necessary to successively apply newly acquired real-time data to an appropriate signal processing circuit. Hence, what is needed is a method for analyzing the acquired intracardiac electrical data in non-real-time, e.g., "off-line", thereby allowing a single acquisition of the data to serve multiple purposes.

An additional problem facing users of products which are regulated by the Federal Drug Administration (FDA), or any other governmental agency, such as pacemakers and programming devices used with pacemakers, is that the appropriate governmental agency must not only initially approve the device itself, but also must approve any modifications subsequently made to the devices, e.g, to any electronic circuitry used within such devices which interfaces in real-time with the patient as the intracardiac electrical data is obtained. Hence, a circuit modification, e.g., to change a filter in order to enhance the observability of cardiac phenomena manifested in the intracardiac electrical data, may require prior FDA approval, which approval may result in a significant delay and expense before it is obtained.

What is thus needed is a system wherein modifications to improve the observability of cardiac phenomena can be readily made in a way which does not affect the hardware or software utilized in real-time to initially acquire the intracardiac electrical data, and hence which does not need to go through an approval cycle. The present invention advantageously addresses the above and other needs.

SUMMARY OF THE INVENTION

In accordance with the present invention, an implantable pacemaker includes conventional means for sensing and telemetering intracardiac electrical signals to a non-implanted diagnostic and programming device remote from the pacemaker. The diagnostic and programming device includes a display for displaying the intracardiac electrical signals in real-time. The diagnostic/programming device further includes sufficient memory for storing the intracardiac electrical signals for subsequent retrieval and analysis.

Such subsequent analysis selectively includes processing means for processing the signals off-line, i.e., not in real-time, using various signal processing strategies, such as digital filtering and frequency domain spectral analysis. As required, the off-line signals may also be recursively processed in order to enhance the detection of a particular physiologic phenomena manifested by, but not readily discerned within, the unprocessed real-time signals. Because the intracardiac electrical signals are processed off-line, i.e., after they have been acquired in real-time, such off-line processing is appropriately referred to as a "post-processing."

Thus, one aspect of the present invention broadly provides for the application of non-real-time signal processing strategies to previously acquired and stored cardiac data. This is in contrast to prior art real-time signal processing strategies wherein cardiac data is processed as it is acquired using specific hardware signal processing circuits, e.g., filters. Advantageously, the off-line signal processing strategies utilized by the present invention are repetitively and recursively applied to the original cardiac data to remove noise, to improve the effective bandwidth, and to provide other benefits not available in real-time. As the various signal processing strategies are invoked to process the cardiac data, the cardiac data is selectively and repetitively displayed subsequent to each processing step, thereby allowing the effects of the particular processing strategies to be readily observed.

Another aspect of the invention provides an enhanced detection system for enhancing the detection of particular physiologic phenomena manifested within an intracardiac electrical signal or a surface electrocardiographic signal. The enhanced detection system in accordance with this aspect of the invention includes four main elements: (1) an implantable pacemaker; (2) a diagnostic system, e.g., external programmer, in signal contact with the implantable pacemaker; (3) a retrieval system for retrieving signals stored in the diagnostic system; and (4) a processing system for analyzing the retrieved signals.

In accordance with another aspect of the present invention, an apparatus for post-processing intracardiac electrical signals is provided. Such apparatus includes: (a) a receiving circuit for receiving the intracardiac electrical signals; (b) an amplifier circuit for amplifying the received intracardiac electrical signals; (c) a memory circuit for storing the amplified intracardiac electrical signals; and (d) a processor circuit for processing the stored intracardiac electrical signals in non-real-time in accordance with at least one of a plurality of signal post-processing strategies.

In accordance with yet another aspect of the present invention, a method for enhancing the analysis of intracardiac electrical signals is disclosed. This method includes: (a) receiving and amplifying the intracardiac electrical signals from a mammalian heart; (b) converting the received and amplified intracardiac electrical signals into digital signals; (c) storing the digital signals; and (d) subjecting the stored digital signals (at a time subsequent to when the intracardiac electrical signals are first received, amplified, converted to digital form, and stored) to at least one signal processing strategy. The signal processing strategy (or strategies) to which the stored digital signals are subjected are advantageously selected to enhance the intracardiac electrical signals so as to reveal characteristics therein which are masked out or otherwise not evident when the intracardiac electrical signals are analyzed in real-time.

It is a feature of the present invention to provide a system and method which uses non-hardware components to enhance the observation and/or analysis of cardiac phenomena, e.g., rare or aperiodic cardiac phenomena which may otherwise be difficult or impossible to observe using conventional hardware processing techniques.

Another feature of the invention allows intracardiac electrical signals to be acquired and recursively processed so as to enhance the detection of particular physiologic phenomena without a requirement of having to preselect a particular hardware filtering or processing strategy prior to the initiation of data collection. Hence, the patient need not be subjected to a test repetition in order to acquire data processed through a more appropriate hardware filter. This, in turn, advantageously reduces patient stress and expense.

It is another feature of the invention to provide such a signal enhancing system which processes sampled cardiac intracardiac electrical signals "off-line", i.e., not in real-time, in accordance with at least one of a collection of signal processing strategies. Such signal processing strategies are advantageously easy and inexpensive to implement, and may be applied, as indicated above, repetitively and/or recursively to the same acquired data without the need of continually subjecting a patient to additional testing in order to acquire additional data under different conditions.

A still further feature of the invention allows selected signal processing strategies to be applied "off-line" to intracardiac electrical signals which have not heretofore been available to process such signals in real-time. This is because the use of such signal processing strategies in real-time is either prohibitively expensive or extremely difficult and complex. Hence, in accordance with this feature of the invention, particular results and insights relative to the informational content of the intracardiac electrical signals are provided which have not previously been available.

Yet another feature of the invention provides for the optimization of the analysis and/or display of intracardiac electrical signals so as to remove unwanted noise therefrom, which noise may mask out important features of the signal being analyzed or displayed. Moreover, such optimization advantageously serves to increase the effective bandwidth of the signal being analyzed or displayed.

Still an additional feature of the invention provides for the rapid, easy and inexpensive off-line modification of a particular intracardiac electrical signal processing strategy, which modifications (because they are performed off-line) may be implemented without requiring prior approval from the FDA or other regulatory agencies.

DESCRIPTION OF THE DRAWINGS

The above and other aspects, features and advantages of the present invention will be more apparent from the following more particular description thereof, presented in conjunction with the following drawings, wherein.

DETAILED DESCRIPTION OF THE PREFERRED EMBODIMENT

The following description includes the best mode presently contemplated for carrying out the invention. This description is not to be taken in a limiting sense, but is made merely for the purpose of describing the general principles of the invention. The scope of the invention should be determined with reference to the claims.

Figure 1:
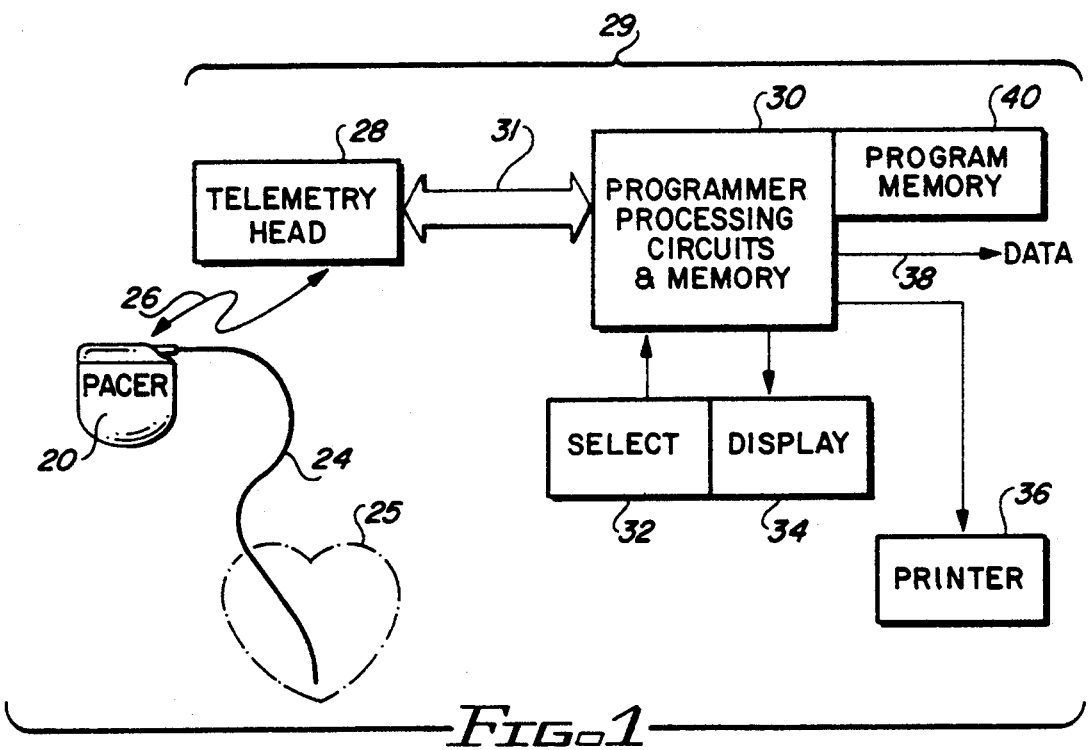
FIG. 1 is a block diagram showing the main components of a pacing/programming system.

Advantageously, the post-processing system herein described includes, with only slight hardware modifications, the same components included within a conventional pacing and programming system. Such a conventional pacing and programming system is shown in FIG. 1. As seen in FIG. 1, the pacing/programming system includes a programmable pacemaker 20, presumably implanted within living tissue, which is in electrical contact with a heart 22 by way of at least one pacemaker lead 24. (It is noted that while the pacemaker 20 in FIG. 1 is presumed to be implanted, it need not be implanted for the pacing/programming system to function. For example, for training purposes, it is quite common to use a programming system with a pacemaker connected to a heart simulator.)

The pacemaker 20 is a self-contained unit which is capable of both sensing natural cardiac activity and providing stimulating pulses to evoke paced cardiac activity. The operating parameters of the pacemaker 20 can be noninvasively programmed using a programmer 29. The programmer 29 includes a telemetry head 28 coupled to processing circuits and memory 30 by way of a suitable connection cable 31. Command signals are received within the pacer 20 over a telemetry link 26. These command signals are generated within the processing circuits 30 of the programmer 29 as selected by an appropriate data/command selection input device 32.

Thus, intracardiac electrical data (e.g., the electrical signals sensed by sensing circuits within the pacer 20, with or without marker data) are received within the programmer 29 over the telemetry link 26. Such intracardiac electrical data may be displayed on a display 34, printed by a printer 36, and/or stored in memory circuits (included as part of the processing circuits 30) within the programmer 29. When the data is stored in this fashion, the intracardiac electrical data is effectively "frozen" so that it can be observed on the display 34 for as long as desired.

Typically, the processing circuits 30 include one or more microprocessors which operate in accordance with a program stored in a program memory 40. Advantageously, some embodiments of the programmer 29 allow the program memory 40 to be detachably replaced with a selected program memory modules, thereby allowing the program carried out by the processing circuits 30 to be readily altered.

Data is output from the processing circuits 30 of the programmer 29 over a data line 38. This data may include intracardiac electrical data received from the pacemaker 20, as well as status data relating to the operation of the pacemaker 20 and the programmer 29. This data may be transferred to a central processing unit (CPU) (not shown) for further processing or logging. This transfer may occur through a direct cable connection, as when the CPU is in close proximity to the programmer 29; or through a modem and a telecommunication network, as when the CPU is located remotely from the programmer 30.

Figure 2:
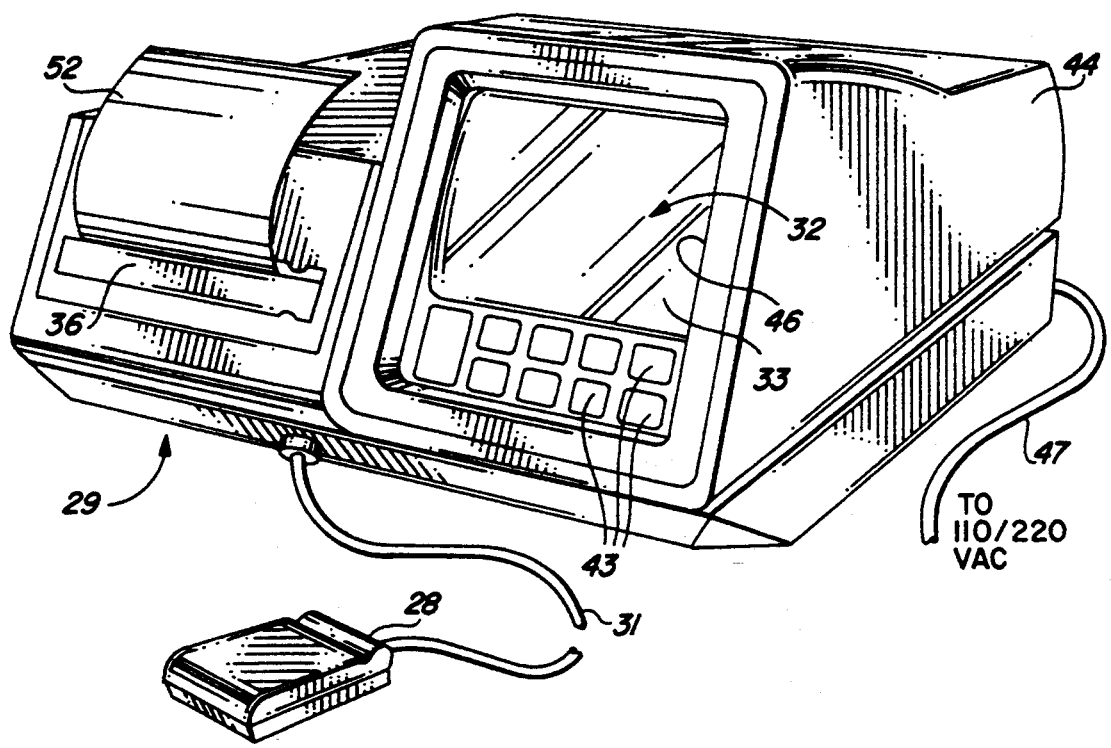
FIG. 2 shows a representative programmer used with the pacing/programming system of FIG. 1.

FIG. 2 shows a representative programmer 29 used with the pacing/programming system of FIG. 1. The particular programmer 29 shown in FIG. 2 includes a housing 44 within which the components of the programmer 29 are housed. For the embodiment shown in FIG. 2, all of the components of the programmer 29 in FIG. 1, except for the telemetry head 28 and the connecting cable 31, are housed within the housing 44. A CRT screen 46, or equivalent display (e.g., LCD display), is used to realize the display 34.

Intracardiac electrical data may thus be displayed on the CRT screen 46. The printer 36 is built into the housing 44. The printer includes an appropriate print head (not shown) which allows the selected signals to be printed on paper 52. A roll of the paper 52 is conveniently stored within the housing 44.

In the embodiment shown in FIG. 2, a transparent touch sensitive membrane 33 overlays the CRT screen 46. This touch sensitive membrane 33 detects a particular section or zone thereon which is touched. Hence, a menu of commands may be displayed on the CRT screen 46, with each selection included in the menu occupying a particular zone or area of the CRT screen 46. The operator, to select a given command, need only touch the area of the CRT screen 46 where the desired command is listed in order to select that command. In this way, the combination of the CRT screen 46 and the touch sensitive membrane 33 function as at least part of the data/command input selection device 32 (FIG. 1). Additional commands may be selected by way of buttons 43 located in an array along the bottom edge of the CRT screen 46.

The programmer 29 is typically powered through a power line cord 47 which is connected to a conventional 50/60 Hz power line at 110 or 220 volts AC. Unlike the pacemaker 20 (which is powered from a battery), the use of 50/60 Hz line power in this manner sometimes creates a problem because the 50/60 Hz power signal may couple through to the intracardiac electrical data or other data. This is particularly a problem because many of the signals included in the intracardiac electrical data have a frequency the same as, or very close to, 50/60 Hz. Thus, the use of a simple filter to remove 50/60 Hz signals from the intracardiac electrical data is generally unacceptable because doing so also removes many of the signals of interest.

Figure 3:
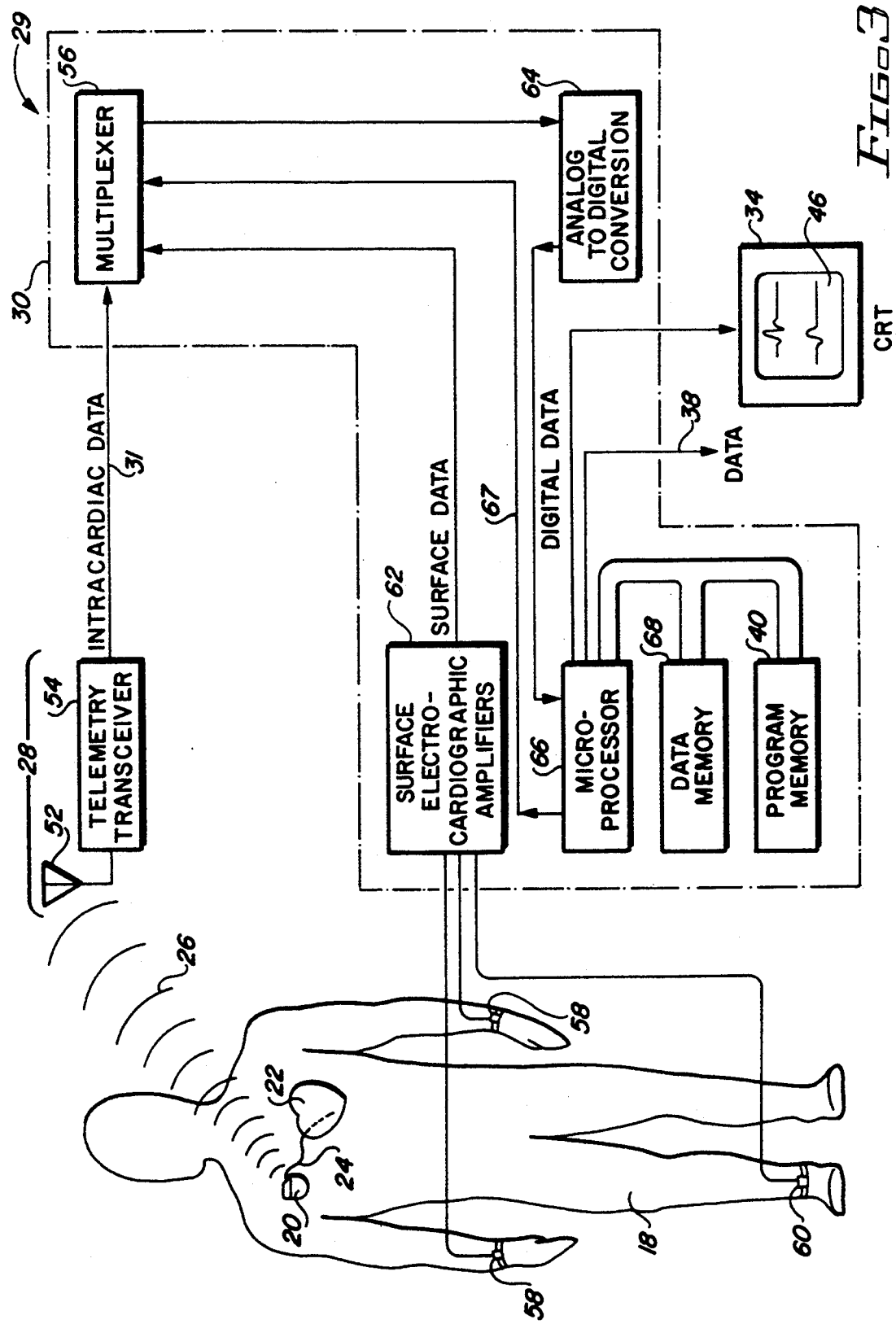
FIG. 3 is a block diagram of the post-processing system of the present invention, which system may be implemented in large measure using the existing hardware components of the pacing/programming system of FIG. 1, which may be the same as shown in the '697 patent to Causey, III et al.

Turning next to FIG. 3, a block diagram of the post-processing system of the present invention is illustrated. Many of the same components shown in FIGS. 1 or 2 are also included in FIG. 3. These same components are referenced with the same reference numerals. As seen in FIG. 3, a patient 18 has a pacemaker 20 implanted (or otherwise carried) in his or her body. This pacemaker 20 is in electrical contact with the patient's heart 24 by way of at least one pacemaker lead 25.

The pacemaker 20 is also in telecommunicative contact with the telemetry head 28 of the programmer 29 by way of the telemetry link 26. The telemetry head 28 includes an antenna 52 and a telemetry transceiver circuit 54. It is the function of the telemetry transceiver circuit 54 to receive intracardiac electrical data over the telemetry link 26 and to preliminarily process this data prior to transferring it to the processing circuits 30 of the programmer 29.

Typically, this preliminary processing involves amplification, and may involve demodulation (if an RF carrier signal is used in sending the data over the telemetry link 26). The transceiver 54 also receives pacemaker commands and data generated by the programmer, converts such commands and/or data into suitable form for transmission over the telemetry link 26, e.g., modulates the same with a suitable carrier signal, and transmits such commands and/or data to the pacemaker 20. Such preliminary processing is fully described in the '697 Causey, III et al. patent, previously incorporated by reference.

For purposes of the present invention, it is the intracardiac electrical data received from the pacer 20 which is of interest. This data, after receipt and processing in the telemetry transceiver 54, is coupled to a multiplexer circuit 56. Also coupled to the multiplexer 56 are surface electrocardiographic data obtained from the surface or skin of the patient 18. That is, skin electrodes 58 and 60, located, e.g., respectively at the wrists and ankle of the patient 18, are connected to surface electrocardiographic amplifiers 62. The surface electrocardiographic amplifiers 62 may be of conventional design, but are preferably located within the processing circuits 30 of the programmer 29 (FIG. 1).

The multiplexer 56 connects a selected one of the telemetered intracardiac electrical data or the surface electrocardiographic data to an analog-to-digital (A/D) converter 64. The A/D converter 64 converts the analog intracardiac electrical data and surface electrocardiographic data into digital data which is supplied to a microprocessor 66. The microprocessor 66 controls the multiplexer 56, over control line 67, so that a desired data source is selected, or so that no data source is selected, at any given time. That is, the microprocessor 66 will always select either the intracardiac electrical data, the surface elecardiographic signal, or no data.

Coupled to the microprocessor 66 is a data memory 68 and the program memory 40. The data memory 68 provides a medium wherein the incoming digital data from the A/D converter 64 is selectively stored for subsequent retrieval and analysis. The program memory 40 provides a medium wherein the control programs of the microprocessor 66 are stored. As indicated above in FIG. 1, it is preferred that the program memory 40 be replaceable (or reprogrammable) so that the controlling programs of the microprocessor 66 can be readily replaced or revised. Data processed by the microprocessor 66 may be selectively displayed on the display device 34, printed on a printer 36 (FIG. 1), or otherwise made available over a data bus 38.

It is noted that while FIG. 3 shows an analog multiplexer 56 (i.e., a multiplexer which selects either the analog telemetered intracardiac electrical data, the analog surface electrocardiographic data, or no data), such is only exemplary. Some embodiments of the invention may perform the A/D conversion prior to selecting it with a digital multiplexer circuit (not shown).

In operation, the system shown in FIG. 3 operates in two basic modes: (1) a data gathering mode; and (2) a data analysis (or post-processing) mode. During the data gathering mode, intracardiac electrical data and/or surface elecardiographic signal is gathered in conventional manner. This data is stored in the data memory 68. This data may also be displayed and or printed as it is gathered.

Advantageously, the intracardiac electrical data and the surface elecardiographic signal may be sampled at appropriate sampling rates so as to allow two channels of data to be displayed on the CRT display 46, both having the same time base, one channel representing the intracardiac electrical data, and the other channel representing the surface elecardiographic signal. The display is thus the same as is commonly done in displaying two separate signals on different channels of an oscilloscope. Having two separate channels of signals displayed in this manner, where each channel originates from the same source (the heart), but each is sensed differently, provides valuable insight into the interpretation of the informational content of such signals.

During the data analysis or post-processing mode, the data previously gathered and stored is processed by the microprocessor 66 in accordance with at least one of a plurality of signal processing strategies aimed at enhancing the detectability and observability of the informational content of the stored signals. Advantageously, the data analysis mode is performed off-line, i.e., not in real-time. Thus, different signal processing strategies may be performed on the same stored data at any time after the data gathering mode has been completed. Hence, the data gathering mode need only be performed once (or at least a minimal number of times), thereby avoiding frequent and repetitive contact with the patient, while the data analysis mode may be carried out as many times as is required or as is desired utilizing the previously stored data.

Figure 4:
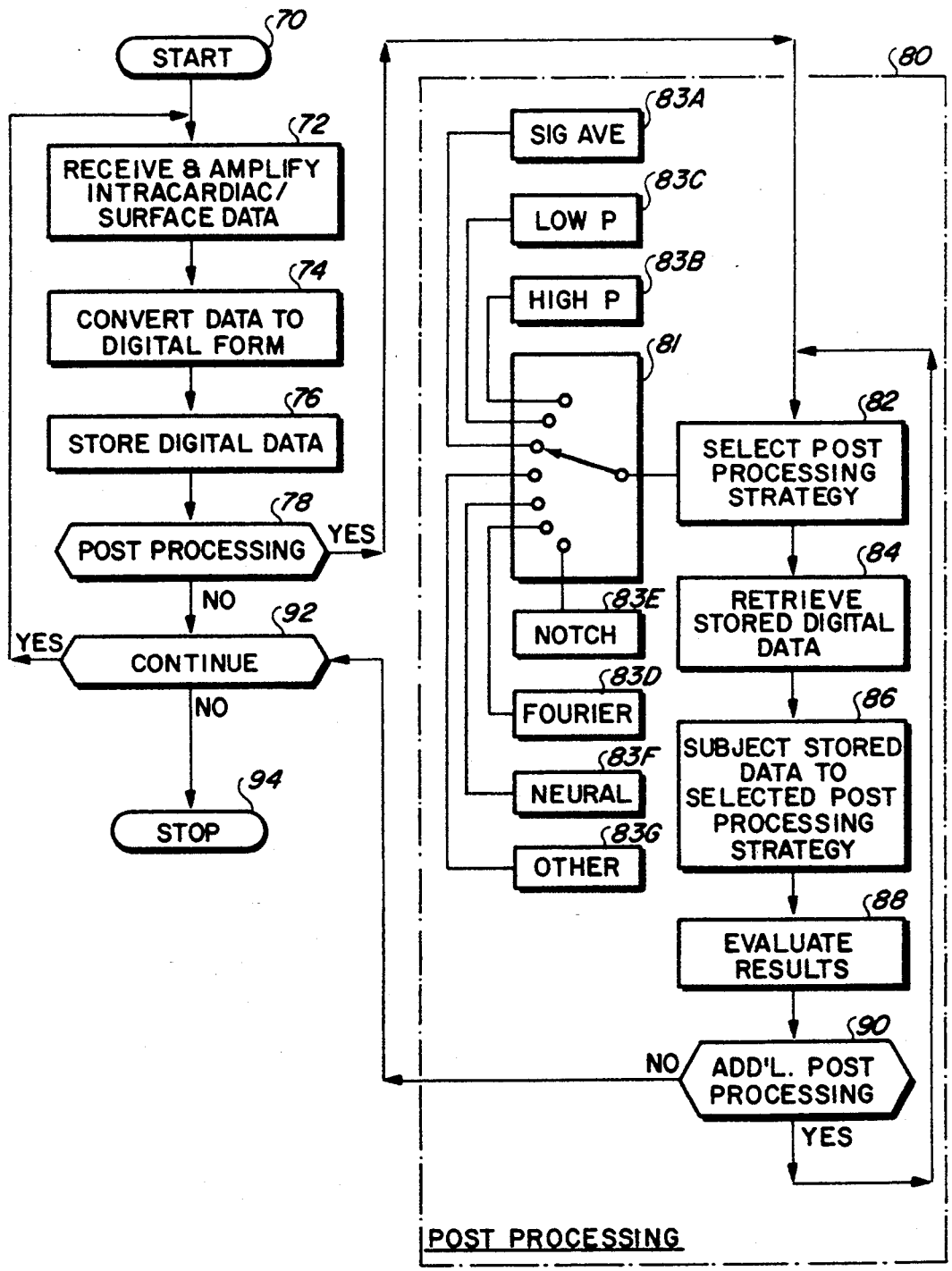
FIG. 4 is a flowchart of the main program used to control the processor of FIG. 3 in accordance with the present invention.

To further illustrate operation of the present invention, reference is next made to FIG. 4 where there is shown a flowchart of a main program which may be used to control the microprocessor 66 of FIG. 3. This main program is stored in at least a portion of the program memory 40. Other portions of the program memory 40 contain programs for the various signal processing strategies which are selectively invoked by the main program. In the flowchart of FIG. 3, "blocks" or boxes, each containing a brief description of a particular action or determination which is made by the program as it is carried out, are illustrated. Each "block" is identified by a reference numeral.

As seen in FIG. 4, once the main control program is started in block 70, the program initiates the data gathering mode by receiving and amplifying the intracardiac electrical data and/or surface electrocardiographic data in block 72. These signals are then converted to digital form in block 74. The converted (digital) signals are then stored in the data memory 68 of FIG. 3 in block 76. Once some data has been thus gathered, a determination is made, at block 78, as to whether post-processing (the data analyzing mode) should commence. If not, then a further determination is made as to whether there is any further data to be gathered in block 92. If so, such further data is received and amplified in block 72, and the data gathering process repeats as described above. If not, the program is then terminated or stopped in block 94.

If a determination is made at block 78 that post-processing of previously stored data is to be performed, the data analysis mode commences in block 80. This data analysis mode includes a first step of selecting a particular post-processing strategy which is to be used to analyze and/or process the stored data in block 82. Such selection is functionally achieved using a selector 81 coupled to a plurality of signal processing strategies, such as, signal averaging (block 83A), high pass filtering (block 83B), low pass filtering (block 83C), Fourier analysis (Block 83D), notch filtering (block 83E), a neural network (block 83F), or other strategy (Block 83G). Then, the stored data is retrieved from the data memory 68 in block 84. Advantageously, the amount of data retrieved from the data memory 68 may be selected to be as much or as little as desired.

Frequently, some cardiac phenomena are manifested in every cardiac cycle, in which case the retrieval of only a few cardiac cycles of data will be all that is required. (A "cardiac cycle" is one beat of the heart, and a normal cardiac cycle typically includes a signal representative of the contraction of the atria, a relatively short delay, a signal representative of the contraction of the ventricles, and a relatively long delay before the cycle begins again with contraction of the atria. A malfunctioning heart may not contain all of these elements in one cycle.)

Sometimes, the cardiac phenomena is aperiodic, or occurs only once, in which case the retrieval of a relatively long sequence of cardiac cycles will be required, with an analysis of each cycle in sequence. In either event, it is of significant benefit to the patient that the post-processing mode need not be performed in real-time, but can be carried forward entirely after the data gathering mode has been completed. Hence, the patient need not be subjected to stressful and/or bothersome and repetitive periods of testing.

After the stored data has been retrieved, the stored data is subjected to the selected post-processing strategy in block 86. The selected strategy processes the data in accordance with a desired function, e.g., low pass filtering, notch filtering, Fourier analysis, etc. The results from the processed data are then evaluated in block 88. Such evaluation may include printing and/or displaying signal waveforms representative of the processed data.

After evaluation of the processed results, a determination is made as to whether additional post-processing should be carried out in block 90. If so, then an appropriate signal processing strategy is selected in block 82, and the post-processing steps are repeated. In this manner, recursive and repetitive analysis of the stored data may be performed, as required or desired, in order to further enhance the detectability of certain features in the data.

If further post-processing is not to be performed in block 90, then the data analyzing mode is concluded, and a final determination is made as to whether any further data is to be gathered in block 92, i.e., if the entire method is to be repeated. If so, then the program repeats beginning with the act of receiving and amplifying additional intracardiac electrical data or surface electrocardiographic data in block 72. If not, then the program terminates in block 94.

One of the advantages of the present invention is that the post-processing system is not limited to the type of post-processing which may be performed. Rather, any or all of a selected group of signal processing strategies may be invoked as best suits the needs of the one doing the analyzing of the intracardiac electrical data and/or surface elecardiographic data.

Each signal processing strategy is defined in an appropriate portion of the control program stored in the program memory. Hence, invoking a different signal processing strategy is as simple as calling up another portion, e.g., subroutine, of the control program stored in the program memory 40, and/or replacing either the contents of the program memory with a new program (in the case where the program memory is of a type which allows new program data to be readily written thereinto, e.g., EPROM, erasable programmable read only memory) or replacing a program memory module with a new program memory module (in the case where the program memory is stored in a replaceable program memory module). Thus, no changes to the hardware are required in order invoke anther processing strategy.

Advantageously, each signal processing strategy may be invoked recursively and/or repetitively as often as desired in order to enhance the ability to analyze the data for a particular feature or phenomena. Further, several different processing strategies may be invoked to operate on the same data, either in parallel or in series. That is, if a "parallel" processing operation is utilized, an initial data set from the data memory is copied into the registers of the microprocessor and subjected to a first signal processing strategy. This first signal processing strategy may be repeated as often as is required until the desired results are achieved.

After completion of the first signal processing strategy, the initial data set is again copied from the data memory and is subjected to a second signal processing strategy. This process repeats, as often as is necessary, until the initial data set has been subjected to each of the data processing strategies, as desired. Such parallel operation may thus be considered as a repetitive process because the same initial data is repeatedly processed in accordance with the desired signal processing strategies.

If a "series" processing operation is utilized, an initial data set from the data memory is copied into the registers of the microprocessor and subjected to a first signal processing strategy. As with the "parallel" processing operation described above, this first signal processing strategy may be repeated as often as is required until the desired results are achieved. Upon completion of the first signal processing strategy, a second signal processing strategy is invoked to operate on the data processed by the first signal processing strategy. That is, the starting data for the second signal processing strategy is the ending data from the first signal processing strategy.

Once the second signal processing strategy is completed, additional signal processing strategies may be invoked, as desired, with each new strategy being invoked using the output data from the operation of the prior strategy as its starting point. Such "series" operation may thus be considered as a recursive process because the data being subjected to the processing is continually processed and refined.

Before describing in more detail some of the signal processing strategies that may be invoked using the present invention, reference will be made to FIGS. 5 and 6 which illustrate some of the hardware used by the system of the present invention. This hardware by itself is not entirely new, but an understanding of the hardware is useful in order to better appreciate the manner in which the various signal processing strategies are carried out.

Figure 5:
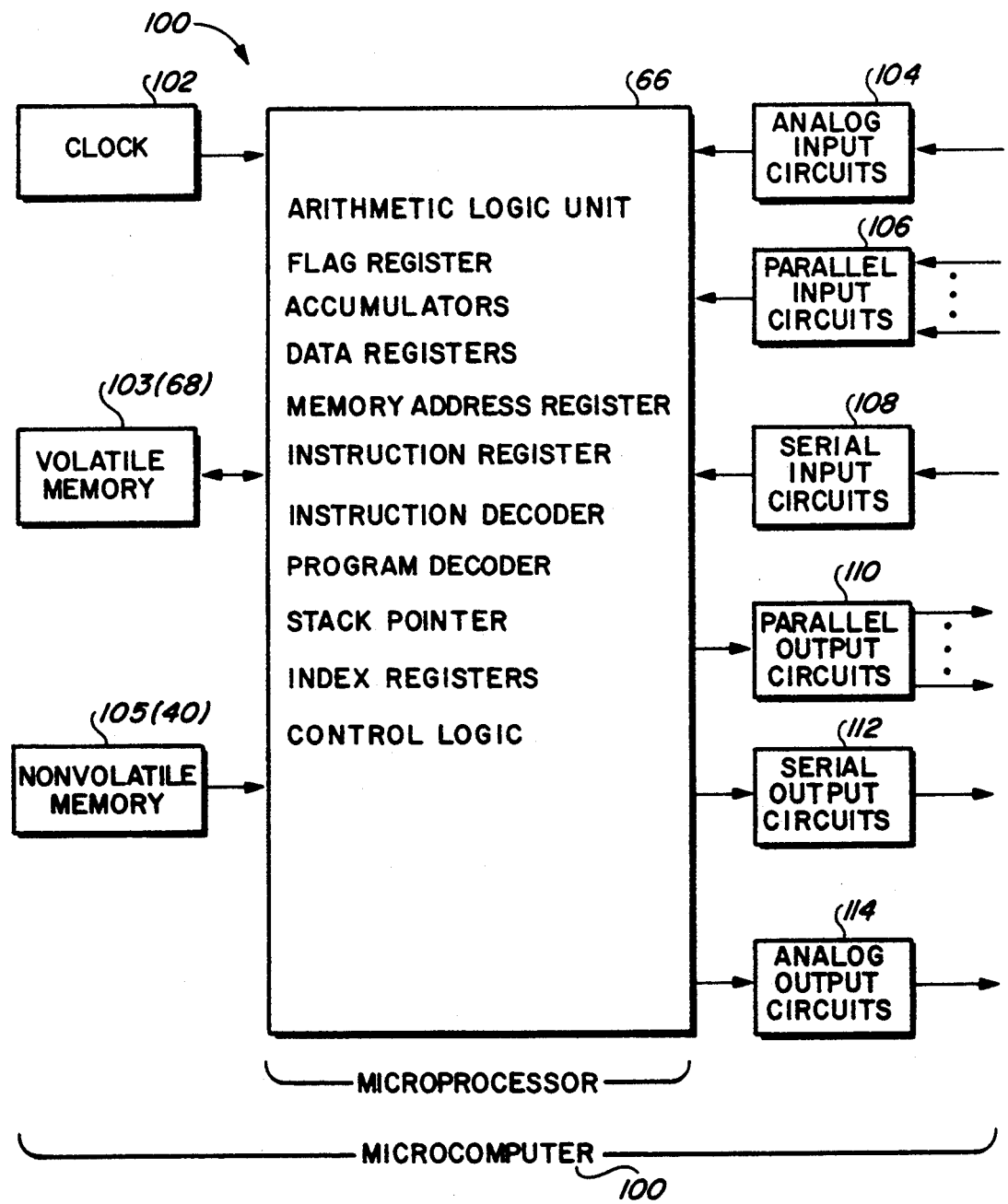
FIG. 5 is a simplified block diagram of a microprocessor-based central processing unit (CPU)

Referring to FIG. 5, there is shown a simplified block diagram of a microprocessor-based central processing unit (CPU), sometimes referred to as a microcomputer 100. The microcomputer 100 includes a microprocessor 66. As is well known and documented in the art, a microcomputer typically includes an arithmetic logic unit, flag registers, accumulators, data registers, memory address registers, instruction registers, instruction decoders, program decoders, stack pointers, index registers, and control logic. The manner of operating a microprocessor is also well documented in the art, and will not be repeated herein. Essentially, the microprocessor carries out a sequence of programmed instructions by selectively retrieving data from memory, loading the data into various registers, performing various arithmetic operations on the data, placing the results of the arithmetic operations back in appropriate registers, and storing the resulting data back in memory.

A key component needed for the operation of the microprocessor 66 is a clock circuit 102. The clock circuit 102 generates a clock signal which synchronizes all of the various data transfers (e.g., loading and clearing registers) that occur within the microprocessor 66. Each operation performed by the microprocessor 66 requires a certain number of clock cycles to be completed. As these operations are performed, delays are built in to the result due to the length of the clock cycle. These delays become important elements to any digital signal processing strategy which is carried out by the present invention, as set forth more fully below.

Other main components used by the microprocessor 66, and forming part of the microcomputer 100, include a volatile memory 103, such as random access memory (RAM). This volatile memory 103 serves as the data memory 68 previously referenced in FIG. 3. Also included within the microcomputer 100 is a nonvolatile memory 105, such as may be realized using ROM or EPROM memory. This nonvolatile memory 105 serves as the program memory 40 previously referenced in FIGS. 1 and 3.

The microcomputer 100 further includes various data input circuits, identified in FIG. 5 as analog input circuits 104, parallel input circuits 106, and serial input circuits 108, as well as various data output circuits, identified in FIG. 5 as parallel output circuits 110, serial output circuits 112, and analog output circuits 114. These various data input and output circuits are intended as functional descriptions.

In practice, the functions performed by such circuits may be combined. For example, the multiplexer (MUX) 56 and A/D converter 64 shown in FIG. 3 perform the function of the analog input circuit 104 and the parallel input circuit 106 shown in FIG. 5. Similarly, it is understood that the output data bus 38 shown in FIG. 3 may include either parallel output data as is provided by the parallel output circuits 110 in FIG. 5, or serial output data as is provided by the serial output circuits 112. The analog output circuits 114 may comprise conventional circuitry needed to drive a CRT display 46, such as is shown in FIG. 3.

Figure 6:
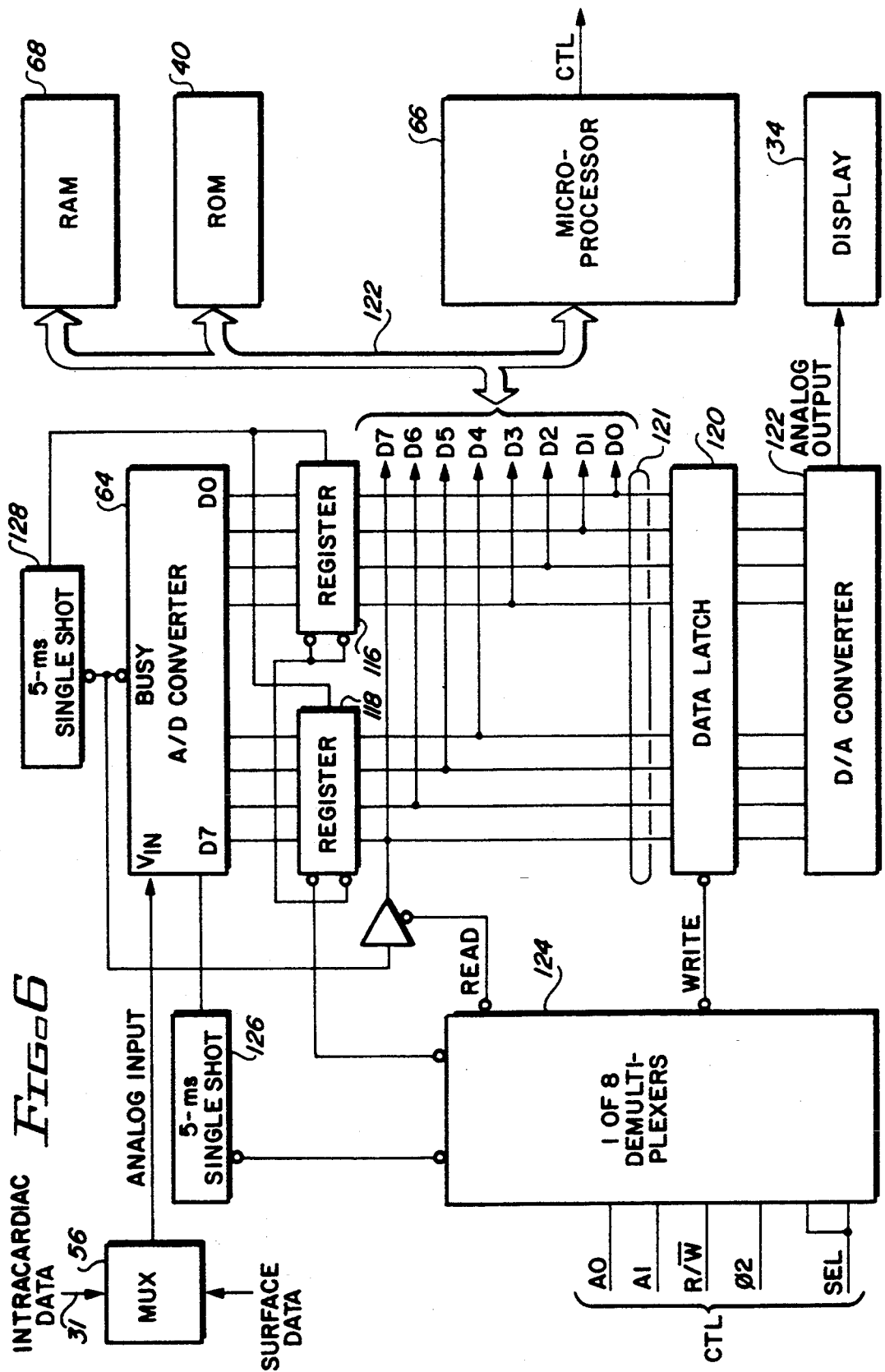
FIG. 6 is a simplified block diagram of the analog input and output circuits used with the post-processing system of the present invention.

FIG. 6 shows a simplified block diagram of the post-processing system of the present invention, particularly illustrating the analog input and output circuits used with the invention. As seen in FIG. 6, the analog intracardiac electrical data and the surface elecardiographic signal are both received at MUX 56, where one is selected and serves as the analog input to an A/D converter 64. The data outputs from the A/D converter 64 are connected to two 4-bit storage registers 116 and 118, making a total of eight bits of resolution which are available. These registers 116 and 118 function as an input data latch.

The A/D converter may be realized using an AD571 integrated circuit (IC) device, commercially available from numerous IC vendors. The storage registers 116 and 118 may be realized using 74173 4-Bit D-Type Registers, also commercially available from numerous IC vendors. The outputs of the registers 116 and 118 are connected to the inputs of an Octal D-Type flip flop 120, used as an output data latch, and may be realized with a 74LS273 IC. The various signal lines between these registers, labeled D0, D1, D2, D3, D4, D5, D6, and D7 comprise a bi-directional data bus 121 which is connected to the microprocessor 66, the program ROM 40, and the data RAM 68.

A digital-to-analog (D/A) converter 122 is connected to the data latch 120, and converts the digital data stored therein to an analog output signal, which analog output signal is connected, e.g., to the display 34. The D/A converter 122 may be a 1408-L8 Converter IC. Control of the input data latches 116 and 118, the output data latch 120, and the A/D converter 64 is controlled by the microprocessor 66 by way of control signals, labeled CTL, which are directed to a 74S138, 1 of 8 demultiplexer IC 124. Single shot circuits 126 and 128, or equivalent, produce five microsecond delays which are required in the operation of the A/D 64.

In operation, the analog input and output circuits shown in FIG. 6 function like two memory locations. The D/A converter 122 is addressed by writing into the first of these memory locations. The A/D converter 64 is addressed by reading from this same address. To initiate a conversion by the A/D 64, a write is done into the second of these memory locations. The A/D converter 64 feeds back a busy flag while it is performing the conversion. The microprocessor must wait for the A/D converter 64 to clear this flag before reading the value. Using the circuitry shown in FIG. 6, conversion takes about 25 microseconds to complete.

As indicated above, one of the advantages of the present invention is the ability to select a particular signal processing strategy as part of the off-line, or post-processing, analysis which is performed. For example, if in gathering intracardiac electrical data or surface elecardiographic data the presence of 60 Hz interference is noted, it has previously been necessary to remove the interference and repeat the gathering of the data in real-time. With the post-processing system of the present invention, however, all that is required is to gather and store the data one time. Then, at a time subsequent to the gathering time, the data is retrieved from storage and subjected to a suitable data processing strategy, such as a digital low pass or notch filter, to remove the interference.

One example of a digital signal process strategy which may be selectively invoked by the present invention is data averaging. That is, the sampled and stored digital data is accessed sequentially, with each sample being averaged with the prior sample, thereby creating, in effect, a second data memory image of the original stored data. This type of averaging creates the effect of having passed the real-time data through a low-pass filter. However, the processing is done off-line, not in real-time, as controlled by the software programs of the microprocessor. Hence, the signal processing strategy may be viewed as a digital (software controlled) low pass filter.

Other types of "digital" filters may also be imposed by the selected signal processing strategy, as discussed below. A filter may be considered as any device which separates one element or class of elements from a mixture of such elements. Nearly every computer program separates special data items from the input data at some point. Thus, for example, a mailing-list program which picks out desired addresses from a data base is, by this broad definition, a filter.

The most common meaning of "filter" in the electronic context, however, is a type of circuit which separates signals at certain frequencies or bands of frequencies from an input spectrum. Filters are typically constructed from hardware components, e.g., resistors, amplifiers, capacitors, and inductors, and such filters operate in the analog domain, i.e., in real-time. A digital computer cannot deal with a continuous stream of input data, and it cannot continuously change its output data.

Rather, the digital circuit receives an input, performs some processing step, and forms an output, all of which requires several clock cycles of "computer time" to complete. However, this "sampled" operation readily lends itself to performing the function of an analog electronic filter, i.e., of separating signals at certain frequencies or bands of frequencies.

To illustrate, it is known that multiplication, addition and subtraction are common computer processes. A delay, whether caused by the built-in delays (e.g., clock cycle) of the computer, or whether programmed delays, is also a common computer process. A delay represents simply the storage of data for a given period of time. To delay a data value by one sample period thus means to simply save that given data value during one computation period for use during the next computation period. Thus, it is possible, for example, to receive as an input one sample of data.

A given delay later, if this sample of data had been passed through a given type of filter, it would have changed by a predictable amount, e.g., decreased in amplitude in accordance with an exponential function. The computer can thus be programmed to perform whatever calculation is required to change a given sample of data as it would be changed after the duration of the delay period. This changed value is then added to the next sample value. One delay later, this "sum" is again processed in an appropriate manner and added to the next sample value. This process repeats for as many samples as are required, producing the same effect on the data as would be produced had the data passed through a given type of filter in real-time.

Numerous algorithms are known in the art for creating various types of digital filters. See, e.g., *Microprocessor Applications Handbook*, by David F. Stout, Chapter 11, "Digital Filters Utilizing Microprocessors" (McGraw-Hill 1982). The use of many of these algorithms are discussed in detail as applied to surface electrocardiographic signals in "Digital Filtering with Applications to Electrocardiogram Processing," by Weaver et al., IEEE Transactions on Audio and Electroacoustics, Vol. Au-16, No. 3, pp. 350–391 (September 1968). The Weaver et al. IEEE article is hereby incorporated herein by reference.

In accordance with the present invention, any desired digital filter or other processing strategy may be evoked during the post-processing of the intracardiac electrical data and/or surface elecardiographic data. In addition to, or in lieu of, a digital low pass filter mentioned above, for example, the selected processing strategy may impose a digital high-pass filter. Such high pass filter, once applied, provides the opportunity to detect and/or observe the relatively higher frequency phenomena of the intracardiac electrical data or surface elecardiographic data, which higher frequency phenomena is typically concealed by low frequency artifacts.

Further, frequency selective band-rejection, or "notch" digital filters may enhance the acquired data by eliminating the effects of interference due to the AC power lines (50/60 Hz), or due to physiologic phenomena such as skeletal muscle activity.

Stored data may further be processed in accordance with the present invention, within the frequency domain by digitally performing a Fourier Transform to display the spectral content of the intracardiac electrical data or surface elecardiographic data. Such a special-content display may provide significant insight into the presence and amplitude of certain frequency components within the stored data, which insight, in turn, will typically help identify the source of such components. Digital Fourier Analysis algorithms are known in the art, see, e.g., *Digital Signal Processing*, by A. Oppenheimer and R. Schafer (Prentice-Hall 1975), which is hereby incorporated by reference It is also to be pointed out that intracardiac electrical data and/or surface elecardiographic data acquired during the gathering phase is typically sampled. As such, certain limitations exist, as expressed by Nyquist, relative to the informational content of the sampled data. The effect of many of these limitations may be minimized by digitally performing a mathematical convolution on the stored data. Hence, digital convolution of the stored data is also one of the signal processing strategies which may be selected while carrying out the post-processing system of the present invention. Digital convolution algorithms are also known in the art, see, e.g., *Digital Signal Processing*, supra.

Advantageously, being able to avoid real-time processing of the intracardiac electrical data and/or surface electrocardiographic signals provides numerous advantages. First, a wide variety of very high performance digital filter algorithms are either published in the literature or are commercially available from numerous software vendors. Any of these algorithms may be selected for use with the post-processing apparatus of the present invention. Such high performance digital filters produce output results which cannot be obtained in real-time absent very complex and expensive signal processing circuits (hardware).

A second advantage of the present system is that valuable data acquired during the data gathering mode may be recursively processed to enhance the detection of physiologic phenomena without a requirement to preselect an appropriate hardware filtering strategy prior to beginning the data gathering mode. Thus, the patient only has to be subjected to the data gathering mode one time, thereby reducing patient stress and expense.

Third, digital filters in many instances provide a level of performance which is unobtainable by practical electronic circuits. Needed computations which are calculated during each sample of the digital filtering process, such as time-consuming floating point calculations, may advantageously be performed without the need for specialized high speed "co-processors," as are typically required in sophisticated real-time signal processing circuits.

Figure 7:
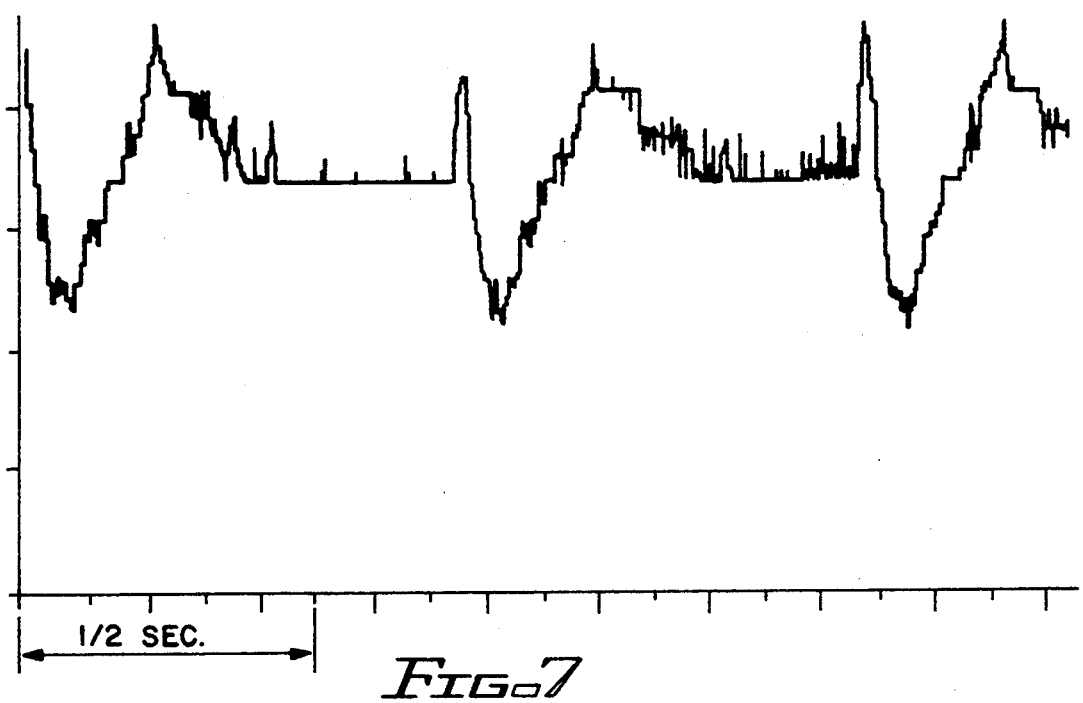
FIG. 7 is a tracing of an atrial intracardiac electrical data before post-processing, with the tracing illustrating both 60 Hz interference and a quantitization error.
Figure 8:
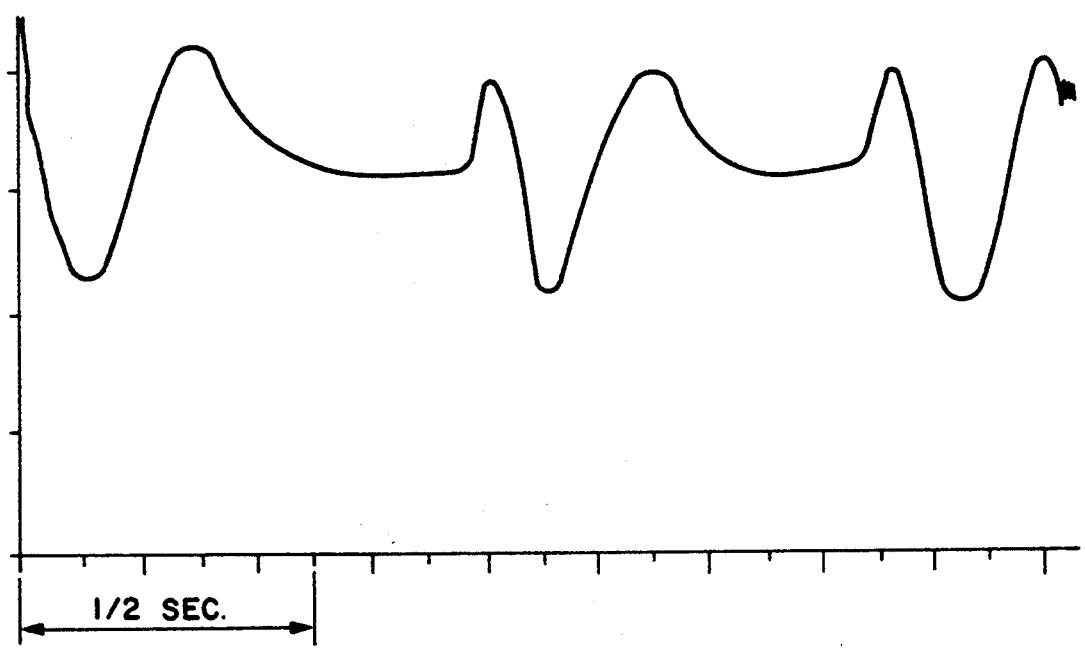
FIG. 8 is a tracing of an atrial intracardiac electrical data after post-processing using the principles of the present invention, with the tracing illustrating the removal of the 60 Hz interference and the quantization error.

Finally, in many instances, the intracardiac electrical signal may actually be enhanced, through the application of appropriate post-processing strategies of the invention, beyond the original hardware design limitations, thereby providing valuable insight into analysis of the intracardiac electrical signal which has heretofore been unavailable. For example, FIGS. 7 and 8 illustrate an atrial intracardiac electrical signal before and after post-processing. Both traces were made at 0.5 mV per division in the vertical direction, with a chart speed of 50.0 mm/sec.

The trace in FIG. 7, which is without post-processing, shows both 60 Hz interference and a quantization error. The trace in FIG. 8, which was digitally post-processed by a 60 Hz notch filter and by a low pass filter to remove both the interference and the error. These figures leave little doubt that the present invention represents a truly significant improvement to the diagnostic capabilities of pacemaker programmers and other cardiac diagnostic devices.

While the invention herein disclosed has been described by means of specific embodiments and applications thereof, numerous modifications and variations could be made thereto by those skilled in the art without departing from the scope of the invention set forth in the claims. For example, while the post-processing of the invention has been disclosed in terms of digital processing (e.g., as performed using a digital microcomputer which is built into the programming/diagnostic device which forms part of the overall pacemaker system), other types of digital processors, including high performance remote CPU's could be used.

Further, it is contemplated that the post-processing could be carried out using artificial neural networks, either as simulated on a digital computer, or as realized using analog circuitry. Indeed, any post-processing of the stored intracardiac electrical data, whether performed on analog or digital data for the purpose of enhancing the detectability of the cardiac phenomena included within the data, could advantageously form part of the present invention.

What is claimed is:

1. A method for analyzing intracardiac electrical signals produced by an implanted pacemaker coupled to a mammalian heart to determine the presence or absence of a particular physiologic phenomena of the mammalian heart, said method comprising the steps of:

(a) receiving intracardiac electrical signals from an implanted pacemaker;
   (b) converting said received intracardiac electrical signals to digital signals;
   (c) storing said digital signals in a memory device;
   (d) retrieving said digital signals from said memory device at a time subsequent to when the intracardiac electrical signals are first received, converted and stored;

(e) electronically enhancing said retrieved digital signals so as to reveal characteristics therein not readily discerned within the intracardiac signal when first received; and (f) electronically displaying the revealed characteristics of the enhanced digital signals, which revealed characteristics provide an indication of the presence of particular physiologic phenomena associated with the mammalian heart to which the implanted pacemaker is coupled.

2. The method, as set forth in claim 1, wherein step (e) of electronically enhancing said retrieved digital signals comprises electronically enhancing a given sequence of retrieved digital signals in a series of recursive steps.

3. The method, as set forth in claim 1, wherein step (e) of electronically enhancing said retrieved digital signals comprises applying said retrieved digital signals to at least one of a group of signal processing strategies, said group of signal processing strategies comprising digital data averaging, digital high pass filtering, digital low pass filtering, digital notch filtering, digital convolution, and Fourier analysis.

4. The method, as set forth in claim 3, wherein step (e) of electronically enhancing said retrieved digital signals comprises applying said retrieved digital signals to a plurality of the signal processing strategies of said group of signal processing strategies.

5. The method, as set forth in claim 3, wherein step (e) of electronically enhancing said retrieved digital signals comprises applying said retrieved digital signals to a 60 Hz notch filter and a digital low pass filter to remove 60 Hz interference therefrom.

6. Apparatus for determining the presence or absence of a particular physiologic phenomena associated with a mammalian heart of a patient to which an implanted pacemaker is coupled, comprising:

means for receiving intracardiac electrical signal from the implanted pacemaker;

conversion means for converting said received intracardiac electrical signal to digital signals;

a memory device;

means for storing said digital signals in said memory device;

means for retrieving said digital signals from said memory device at a time subsequent to when the intracardiac electrical signals are first stored in said memory device;

enhancing means for electronically enhancing said retrieved digital signals; and display means for displaying the electronically enhanced signals so as to reveal characteristics therein not readily discerned within the intracardiac signal when first received, which characteristics provide an indication of a particular physiologic phenomena associated with said mammalian heart.

7. The apparatus as set forth in claim 6, further including:

means for receiving surface electrocardiographic signals from the patient; and multiplexer means for coupling a selected one of said received electrocardiographic or intracardiac electrical signal to said conversion means;

whereby either said received surface electrocardiographic signals or said received and amplified intracardiac electrical signal may be enhanced by said enhancing means.

8. The apparatus, as set forth in claim 7, wherein said multiplexer means couples said received electrocardiographic signals to said conversion means for a first sample time, and said received and amplified intracardiac electrical signal to said conversion means for a second sample time, whereby both said electrocardiographic and intracardiac electrical signal may be enhanced by said enhancing means.

9. The apparatus, as set forth in claim 6, further wherein said enhancing means comprises at least one of a digital high pass filter, a digital low pass filter, a digital notch filter, a digital convolution device, or a Fourier analysis device.

10. The apparatus, as set forth in claim 9, wherein said display means comprises:

means for converting said enhanced, retrieved digital signals to an analog signal; and display means for displaying a graphical representation of said analog signal.

11. Apparatus for analyzing intracardiac electrical signals produced by an implantable pacemaker comprising:

transceiver means for transmitting control commands to and receiving transmitted intracardiac electrical signal from said implantable pacemaker, said control commands causing said implantable pacemaker to transmit intracardiac electrical signals, said transceiver means further comprising amplifier means for amplifying said intracardiac electrical signal received from said implanted pacemaker;

conversion means for converting said received and amplified intracardiac electrical signal to digital signals;

a data memory; and control means for storing said digital signals in said data memory and retrieving said digital signals from said data memory at a time subsequent to when the intracardiac electrical signals are first stored in said memory device, said control means comprising processing means for electronically enhancing said retrieved digital signals so as to reveal characteristics therein not readily discerned within the intracardiac electrical signal when first received by said transceiver means.

12. The apparatus, as set forth in claim 11, further including:

means for receiving and amplifying surface electrocardiographic electrical signals; and multiplexer means for coupling a selected one of said received electrocardiographic or intracardiac electrical signal to said conversion means;

whereby either said received surface electrocardiographic signals or said received intracardiac electrical signal may be converted by said conversion means and enhanced by said processing means.

13. The apparatus, as set forth in claim 11, wherein said processing means includes means for subjecting said retrieved digital signals to at least one of a digital high pass filter, a digital low pass filter, a digital notch filter, a digital convolution device, or a Fourier analysis device.

14. The apparatus, as set forth in claim 13, wherein said display means comprises:

means for converting said digital signals after being enhanced by said processing means to an analog signal; and display means for displaying a graphical representation of said analog signal.

15. Apparatus for determining the presence or absence of a particular physiologic phenomena associated with a patient having an implanted pacemaker, said pacemaker having means for sensing and transmitting intracardiac electrical data signals, said apparatus comprising:
- a telemetry transceiver that receives the intracardiac electrical data signals from the implanted pacemaker;
- an analog-to-digital (A/D) converter connected to said telemetry transceiver that converts the received intracardiac electrical data signals to digital data signals;
- a data memory that stores digital data signals;
- a microprocessor coupled to said A/D converter and data memory;
- a program memory coupled to said microprocessor, said program memory having a control program stored therein that controls said microprocessor so as to store said digital data signals in said data memory when first received from said A/D converter, and to retrieve said digital data signals from said data memory at a time subsequent to when the digital data signals are first stored in said data memory, said control program further controlling said microprocessor so as to electronically enhance the digital data signals retrieved from said data memory; and
- a display device coupled to said microprocessor, said display device including means for displaying a graphical representation of the enhanced digital data signals to reveal characteristics therein not readily discerned within the intracardiac electrical data signals received by said telemetry receiver, which characteristics provide an indication of a particular physiologic phenomena associated with said patient.

16. The apparatus, as set forth in claim 15, further including:
- a plurality of skin electrodes adapted for attachment to the skin of said patient;
- a surface electrocardiographic amplifier attached to said skin electrodes that receives a surface electrocardiographic signal from the plurality of skin electrodes; and
- a multiplexer circuit controlled by said microprocessor and connected to said surface electrocardiographic amplifier and said telemetry transceiver that includes means for coupling a selected one of said received surface electrocardiographic signal or said intracardiac electrical data signal to said A/D converter;
- whereby either said received surface electrocardiographic signal or said received intracardiac electrical data signal may be stored in said data memory and subsequently electronically enhanced by said microprocessor.

17. The apparatus, as set forth in claim 16, wherein said multiplexer circuit couples said received surface electrocardiographic signal to said A/D converter for a first sample time, and said received intracardiac electrical signal to said A/D converter for a second sample time, whereby samples of both said surface electrocardiographic signal and intracardiac electrical signal may be stored in said data memory and subsequently retrieved for enhancement by said microprocessor.

18. The apparatus, as set forth in claim 17, further including a display device coupled to said microprocessor that displays a graphical representation of the electronically enhanced digital data signals.

19. The apparatus, as set forth in claim 16, wherein the microprocessor includes means for electronically enhancing the digital data signals retrieved from the data memory by subjecting said digital data signals to at least one of the signal processing strategies comprising: digital data averaging, digital high pass filtering, digital low pass filtering, digital notch filtering, digital convolution or Fourier analysis.

20. A system for enhancing the detection of a particular physiologic phenomena manifest within an intracardiac electrical signal comprising:
- an implantable pacemaker that includes means for sensing intracardiac electrical signal and means for telemetering such intracardiac electrical signal to a non-implanted location remote from the implantable pacemaker; and
- an external programmer in signal contact with said implantable pacemaker, said external programmer including:
  - a telemetry receiver circuit that receives the intracardiac electrical signal telemetered from the implantable pacemaker
  - a data memory,
  - a storage system that stores the intracardiac electrical signal received by the telemetry receiver in said data memory,
  - a retrieval system that selectively retrieves the intracardiac electrical signal previously stored in the data memory, and
  - a processing system that processes the retrieved intracardiac electrical signal in accordance with at least one of a plurality of signal processing strategies, said signal processing strategies being selected to enhance the detection of a particular physiologic phenomena manifested within the intracardiac electrical signal;
  - display means for displaying the intracardiac signals after being processed by said processing system;
  - whereby said intracardiac electrical signal is processed at a time subsequent to their receipt within the external programmer, thereby enabling said signal processing strategies to be carried out offline (not in real-time), thereby facilitating the repetitive application of said signal processing strategies so as to better enhance the detection of the particular physiologic phenomena manifested within the intracardiac electrical signal.

21. The system, as set forth in claim 20, wherein said external programmer further includes:
- surface electrocardiographic amplifiers for receiving surface electrographic signals; and
- a multiplexer circuit for selectively connecting either said surface electrographic signals received by said surface electrocardiographic amplifiers or said intracardiac electrical signal received by said telemetry receiver to said storage system, whereby either said surface electrographic signals or said intracardiac electrical signal may be stored in said data memory.

22. The system, as set forth in claim 21, wherein said intracardiac electrical signal and said surface electrographic signals comprise analog signals, and wherein said external programmer further includes an analog-to-digital (A/D) converter that converts the surface electrographic signals and the intracardiac electrical signal to digital signals prior to having said signals stored in said data memory.

23. The system, as set forth in claim 22, wherein said A/D converter includes means for converting the analog intracardiac electrical signal and surface electrographic signals to digital signals at a prescribed sampling rate.

24. The system, as set forth in claim 21, wherein said storage system, retrieval system, and processing system comprise:
 a data bus connected to said data memory and A/D converter;
 a processing unit connected to the data bus;
 a read-only memory (ROM) connected to the data bus, said ROM having a program loaded therein that controls the operation of said processing unit so as to: (a) selectively store the digital signals output from the A/D converter in said data memory, (b) selectively retrieve the digital signals stored in the data memory at a time subsequent to when they are first stored therein, and (c) process the retrieved digital signals offline in accordance with one of said signal processing strategies.

25. The system, as set forth in claim 24, wherein said external programmer further includes:
 a digital-to-analog (D/A) converter coupled to said data bus that converts digital data appearing on said data bus to an analog signal appearing on an output port of said D/A converter; and
 a display connected to the output port of said D/A converter that provides a graphical display of the analog signal appearing on the output port of the D/A converter;
 the program loaded in said ROM further controlling said processing unit so as to selectively place the retrieved digital signals processed by the processing unit on the data bus for conversion to analog signals by said D/A converter, with said analog signals being graphically displayed by said display, the display of said analog signals providing an alternate technique for detecting the particular physiologic phenomena manifested within the intracardiac electrical signal.

26. The system, as set forth in claim 20, wherein said at least one signal processing strategy used by said processing system is selected from the group comprising digital averaging, digital high pass filtering, digital low pass filtering, digital notch filtering, digital convolution or Fourier analysis.

27. A method for analyzing intracardiac electrical signals comprising the steps of:
 (a) sensing intracardiac electrical signals with an implanted pacemaker, said implanted pacemaker having pacing/sensing leads in contact with a patient's heart;
 (b) telemetering said intracardiac electrical signals to a non-implanted receiver;
 (c) receiving and amplifying the intracardiac electrical signals at the non-implanted receiver;
 (d) electronically holding a selected sample of the received and amplified intracardiac electrical signals for subsequent off-line processing;
 (e) electronically processing the held sample of the intracardiac electrical signals pursuant to a selected processing strategy, the processed intracardiac electrical signal sample providing an indication of characteristics in the intracardiac electrical signal not readily discernable using real-time processing.

28. The method, as set forth in claim 27, wherein said received and amplified intracardiac electrical signals comprise analog signals, and wherein step (d) comprises converting said received and amplified intracardiac electrical signals to digital signals on a sampled basis, and storing said digital signals as digital sampled signals in a data memory.

29. The method, as set forth in claim 28, wherein step (e) includes retrieving said digital sampled signals from said data memory and subjecting said retrieved digital sampled signals to a first signal processing strategy to produce a first result, subjecting said first result to a second signal processing strategy to produce a second result, and so on, with the result of a preceding signal processing strategy being used as starting data for a next signal processing strategy, until a prescribed number of different signal processing strategies have been used.

30. The method, as set forth in claim 29, wherein the prescribed number of different signal processing strategies used in step (e) includes a plurality of signal averaging, low pass filtering, high pass filtering, notch filtering, convolution and Fourier analysis.

31. The method, as set forth in claim 27, wherein step (e) includes retrieving said digital sampled signals from said data memory, subjecting said retrieved digital sampled signals to said selected processing strategy to produce output data, reapplying said output data to said selected processing strategy to produce new output data, and continuing to reapply said new output data to said selected processing strategy for a prescribed number of iterations.

32. The method, as set forth in claim 31, wherein the prescribed number of iterations comprises at least two.

33. The method, as set forth in claim 31, wherein the electronic processing carried out in step (e) includes processing the held sample of the intracardiac electrical signals in accordance with at least one of: signal averaging, low pass filtering, high pass filtering, notch filtering, convolution or Fourier analysis.

34. The method, as set forth in claim 27, further including:
 sensing surface electrocardiographic signals from a patient;
 receiving and amplifying the sensed surface electrographic signals at the non-implanted receiver; and
 electronically holding a selected sample of either the received and amplified intracardiac electrical signals or surface electrographic signals for subsequent off-line processing.

35. The method, as set forth in claim 34, wherein the step of electronically holding includes electronically holding said received and amplified intracardiac electrical signals and said surface electrocardiographic signals on an alternating basis, to allow subsequent off-line processing of two channels of data.

* * * * *